United States Patent [19]

Berning et al.

[11] 4,330,484
[45] May 18, 1982

[54] DIASTEREOMERIC SALTS OF MALIC ACID AND 2-AMINOBUTANOL, AND PROCESS FOR THE RESOLUTION OF RADEMIS MAIC ACID

[75] Inventors: Wilfried Berning, Kirchheimbolanden; Hardo Siegel, Speyer, both of Fed. Rep. of Germany

[73] Assignee: BASF Aktiengesellschaft, Fed. Rep. of Germany

[21] Appl. No.: 166,576

[22] Filed: Jul. 7, 1980

[30] Foreign Application Priority Data

Aug. 22, 1979 [DE] Fed. Rep. of Germany ....... 2933895

[51] Int. Cl.³ ...................... C07C 91/04; C07B 19/00
[52] U.S. Cl. ............................. 260/501.17; 562/401; 564/303
[58] Field of Search ............................. 562/401, 582; 260/501.17, 583 DD; 564/303

[56] References Cited

U.S. PATENT DOCUMENTS

| | | | |
|---|---|---|---|
| 3,116,332 | 12/1963 | Sullivan | 564/303 |
| 3,401,194 | 9/1968 | Zoya | 564/303 |
| 3,553,257 | 1/1971 | Halmos et al. | 260/501.17 |
| 3,579,586 | 5/1971 | Zoya | 564/303 |
| 3,579,587 | 5/1971 | Zoya | 564/303 |
| 3,855,283 | 12/1974 | Cohen et al. | 564/303 |

FOREIGN PATENT DOCUMENTS 639304 4/1962 Canada.

OTHER PUBLICATIONS

Toxicology 8 (1977), pp. 263–274 and pp. 333–346.
G. J. W. Bremer, Rec. Trav. Chim. 4, (1885), p. 181.
B. Holmberg, Z. Phys. Chem. 137 (1928), pp. 20–29.

Primary Examiner—Nicky Chan
Assistant Examiner—Vera C. Clarke
Attorney, Agent, or Firm—Keil & Witherspoon

[57] ABSTRACT

Racemic malic acid can be fractionally crystallized, as a diastereomeric salt pair, from alcoholic solution or aqueous-alcoholic solution by using an optical antipode of 2-amino-butan-1-ol.

5 Claims, No Drawings

DIASTEREOMERIC SALTS OF MALIC ACID AND 2-AMINOBUTANOL, AND PROCESS FOR THE RESOLUTION OF RADEMIS MAIC ACID

The present invention relates to a process for the resolution of racemic malic acid. In particular, the process provides L(−)-malic acid.

Malic acid is employed in large quantities in the food industry as a characteristic acid flavor. Synthetic D,L-malic acid, which is easily obtainable, is especially used for this purpose. On the other hand, natural L(−)-malic acid can only be isolated at great expense from suitable fruit, via the sparingly soluble calcium salts of the acid.

In spite of the substantial difference in price between the D,L-acid and the L(−)-acid, the demand for optically active malic acid has been constantly rising, following the general trend toward using only those food additives which occur in natural foods. In this context, a recent investigation of the chemically related system of tartaric acid/racemic acid (Toxicology 8 (1977), 263–274 and 333–346), in which the optically active natural form and the racemic synthetic form were found to have different toxicities, is of great importance.

The resolution of the racemate of D,L-malic acid by using the base cinchonine is described in the literature (G. J. W. Bremer, Rec. Trav. Chim. 4 (1885), 181). After numerous recrystallizations, L(−)-malic acid is obtained in poor optical purity.

(+)-Phenylethylamine has also been used for separating the antipodes of D,L-malic acid (B. Holmberg, Z. Phys. Chem. 137 (1928), 21). The poor optical purity of the malates necessitated repeated purification by recrystallization. The yield was about 62%.

A feature of all the conventional racemate resolution methods by fractional crystallization of diastereomeric malates is that the bases employed are very expensive and that, because of their high molecular weights, they must be used in large amounts.

It is an object of the present invention to provide a process for the racemate resolution of D,L-malic acid, which is based on a cheap resolving reagent having a very low molecular weight and a high efficiency.

We have found, surprisingly, that D,L-malic acid, preferably in a low molecular weight alcohol containing less than 40% of water, forms with optically active 2-amino-butan-1-ol a sparingly soluble diastereomeric salt, which crystallizes out and can be separated from the mother liquor. The optically active acids and the 2-aminobutanol can be obtained from the respective diastereomeric salts, contained in the crystals and in the mother liquor, by means of acids and bases, using conventional methods.

Optically active R(−)-2-amino-butan-1-ol can easily be obtained, for example by the method of German Pat. No. 1,243,206, from racemic 2-amino-butan-1-ol by resolving the racemate, using natural (+)-tartaric acid. It is highly resistant to racemization and can be purified inexpensively by distillation. It has a comparatively low molecular weight and possesses excellent solubility in the solvents employed for resolving the racemate. After the racemization has been successfully carried out, it can be recovered by conventional methods and recycled to the process.

Since the diastereomeric salts of (−)-malic acid described in the literature are only formed with bases which possess large substituents and hence have high molecular weights, it is surprising that the reaction, according to the invention, of D,L-malic acid with optically active aminobutanol is capable of giving an overall yield of from 80 to 90% of pure optically active malate, substantially regardless of the solvent used.

By selecting a suitable concentration it is possible to bring about the precipitation of a diastereomeric salt pair which, even without recrystallization, possesses high optical purity suitable for further processing. Solvents which are effective over a wide concentration range are methanol, ethanol and other low molecular weight alcohols, preferably not containing an excessive amount of water. The (−)(−)— or (+)(+)-salt pair preferentially crystallizes out from these solvents.

For example, if R(−)-2-aminobutanol is employed, the (−)(−)-salt pair crystallizes out from a low molecular weight alcohol containing less than 40, preferably less than 20, % by weight of water. The best conditions for achieving adequate purity and yield can easily be determined by varying the concentration. The reaction is preferably carried out at room temperature—the mixture becomes warm as a result of the exothermicity of the reaction—and is stirred initially to produce better mixing. Seeding with (−)(−)-salt is advantageous, in that it produces better crystallization. Under identical conditions, S(+)-aminobutanol gives the diastereometric (+)(+)-salt pair. To resolve the racemate, 0.5 or more equivalents of the optically active aminobutanol may be used per mole of D,L-malic acid. Preferably, equimolar amounts of malic acid and aminobutanol are used, since this gives the highest yields.

EXAMPLE 890 g of R(−)-2-aminobutan-1-ol are added to a solution of 1,340 g of D,L-malic acid in 1,784 ml of anhydrous methanol at 25° C. After the reaction has subsided and the mixture has cooled to room temperature, 1,015 g of solid R(−)-aminobutanol (−)-malate are isolated ($[\alpha]_D^{25} = -7.1$, c=5 g/110 ml in methanol), indicating 91% purity. To recover the acid and base, two equivalents of 55% strength potassium hydroxide solution are added to the solid salt and the resulting upper phase, which contains aminobutanol, is separated from the lower phase (which contains dipotassium malate). 860 g of pure R(−)-2-aminobutanol are recovered by distillation of the upper phase. The aqueous solution of the dipotassium malate is converted to the free acid by passing it over a strongly acidic ion exchanger in the H+ form (polystyrenesulfonic acid; the particular material used is Lewatit S 100, from Bayer AG). To isolate L(−)-malic acid, the issuing solution is concentrated under reduced pressure to an acid content of 60%. After filtration, which gives 9 g of impure (i.e. more or less racemic) malic acid, 601 g of optically pure L(−)-malic acid ($[\alpha]_D^{25} = 25.7°$, c=5 g/100 ml in pyridine) are isolated by spray-drying.

The mother liquor from the racemate resolution is worked up similarly, after stripping off the solvent. On concentrating the solution which has been treated with the ion exchanger, 41 g of impure D(+)-malic acid are first isolated; subsequent spray-drying of the solution gives 650 g of optically pure (+)-antipode ($[\alpha]_D^{25} = +25.3°$; c=5 g/100 ml in pyridine).

Using the process according to the invention, with R(−)-aminobutanol, pure D(+)-malic acid is furthermore obtained by stripping the solvent from the mother liquor of the racemate resolution and then precipitating, from the mother liquor, pure R(−)-aminobutanol (+)-malate, which can be split, by conventional methods, into R(−)-aminobutanol and D(+)-malic acid. This D(+)-malic acid can be used for the resolution of racemic aminobutanol, whereby the important drug intermediate S(+)-2-aminobutan-1-ol can be obtained simply and in a particularly pure form.

EXAMPLE 2

445 g of D,L-2-amino-butan-1-ol are added to a solution of 670 g of D(+)-malic acid in 850 ml of methanol at 25°. When the reaction has subsided, 508 g (91%) of S(+)-aminobutanol (+)-malate ($[\alpha]_D^{25} = +7.25$, c=5 g/100 ml in methanol) are isolated at room temperature. To obtain the base and the acid, the entire quantity of the salt is mixed with two mole equivalents of 55% strength potassium hydroxide solution and the upper (aminobutanol) phase is separated from the lower (dipotassium malate) phase. Distillation of the upper phase gives 200 g (90%) of S(+)-2-aminobutan-1-ol ($[\alpha]_D^{20} = +9.94°$, undiluted). D(+)-Malic acid is recovered, similarly to Example 1, from the aqueous dipotassium malate phase by passing it over a strongly acidic ion exchanger. 327 g (98%) of D(+)-malic acid ($[\alpha]_D^{25} = +25.3°$, c=5 g/100 ml in pyridine) are isolated.

The diastereometric salts obtained are washed with a small amount of methanol, and after this treatment exhibit the following specific optical rotation (in solution):

(−)-Aminobutanol (−)-malate $[\alpha]_D^{25} = 7.3$; c=5 g/100 ml in methanol (+)-Aminobutanol (+)-malate $[\alpha]_D^{25} = +7.25$; c=5 g/100 ml in methanol (−)-Aminobutanol (+)-malate $[\alpha]_D^{25} = 3.4$; c=5 g/100 ml in methanol After working up, (−)- and (+)-malic acid are obtained in 97% optical purity.

(−)-Malic acid $[\alpha]_D^{25} = −25.7°$ (c=5 g/100 ml in pyridine)

(+)-Malic acid $[\alpha]_D^{25} = +25.3°$ (c=5 g/100 ml in pyridine)

The following data were found for the salts—which had not previously been described—of R(−)- and S(+)-2-aminobutan-1-ol with D(+)- and L(−)-malic acid:

(a) R(−)-Aminobutanol (−)-malate
Melting point (after recrystallization from ethanol)=115° C.
$[\alpha]_D^{25} = −7.3$ (c=5 g/100 ml in methanol)
$^1$H-NMR (D$_2$O): δ(TMS): 0.90 (t, 3); 1.55 (m, 2); 2.65 (m, 2); 3.12 (m, 1); 3.6 (m, 2); 4.25 (m, 1)
Elementary analysis for C$_8$H$_{17}$NO$_6$ (223.23): calculated: C:43.05%; H:7.68%; N:6.27%. found: C:43.01%; H:7.62%; N:6.30%.

(b) S(+)-Aminobutanol (+)-malate
Melting point (after recrystallization from ethanol)=115°–116° C.
$[\alpha]_D^{25} = +7.25$ (c=5 g/100 ml in methanol)
$^1$H-NMR (D$_2$O): δ(TMS): 0.90 (t, 3); 1.55 (m, 2); 2.65 (m, 2); 3.13 (m, 1); 3.6 (m, 2); 4.25 (m, 1)
Elementary analysis for C$_8$H$_{17}$NO$_6$ (233.26): calculated: C:43.05%; H:7.68%; N:6.27%. found: C:43.06%; H:7.65%; N:6.24%.

(c) R(−)-Aminobutanol (+)-malate
Melting point=24° C.
$[\alpha]_D^{25} = −3.4°$, c=5 g/100 ml in methanol
$^1$H-NMR (D$_2$O): δ(TMS): 0.90 (+, 3); 1.55 (m, 2); 2.65 (m, 2); 3.13 (m, 1); 3.6 (m, 2); 4.85 (m, 1)
Elementary analysis for C$_8$H$_{17}$NO$_6$ (223.26): calculated: C:43.05%; H:7.68%; N:6.27%. found: C:43.08%; H:7.71%; N:6.31%.

(d) S(+)-Aminobutanol (−)-malate
The physical and analytical behavior of this substance did not, except for the sense of rotation and within the limits of error, differ from its optical enantiomer.

We claim:

1. The diastereomeric salts of R(−)-2-aminobutan-1-ol and S(+)-2-aminobutan-1-ol with D(+)- and L(−)-malic acid.

2. A process for resolving malic acid by fractional crystallization of diastereometric salts of malic acid comprising reacting D,L-malic acid with optically active 2-aminobutan-1-ol in solution, separating the crystallized diastereomeric salt from the mother liquor and recovering D(+)-malic acid, L(−)-malic acid and optically active 2-aminobutan-1-ol from said crystallized salt and said mother liquor.

3. The process of claim 2, wherein R(−)-2-aminobutan-1-ol is used.

4. The process of claim 2, wherein the solvent used is a low molecular weight alcohol containing less than 40% by weight of water.

5. The process of claim 2, wherein at least 0.5 equivalents of 2-aminobutan-1-ol is used per mole of malic acid.

* * * * *